(12) United States Patent
O'Keefe et al.

(10) Patent No.: US 7,670,332 B2
(45) Date of Patent: *Mar. 2, 2010

(54) ANTI-REFLUX DRAINAGE DEVICES AND METHODS

(75) Inventors: Christopher R. O'Keefe, Holliston, MA (US); John O. McWeeney, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 284 days.

This patent is subject to a terminal disclaimer.

(21) Appl. No.: 11/174,618

(22) Filed: Jul. 6, 2005

(65) Prior Publication Data

US 2005/0246038 A1 Nov. 3, 2005

Related U.S. Application Data

(63) Continuation of application No. 09/973,660, filed on Oct. 9, 2001, now Pat. No. 6,921,378.

(51) Int. Cl.
*A61M 27/00* (2006.01)

(52) U.S. Cl. .............................. 604/544; 604/8; 604/9; 604/249; 604/288.03; 604/537; 604/540; 600/29; 600/30; 600/31; 623/23.64; 623/23.65; 623/23.68; 623/23.7; 137/854

(58) Field of Classification Search .............. 604/8, 604/9, 249, 288.03, 537, 540, 544; 600/29–31; 623/23.64, 23.65, 23.68, 23.7; 137/854; 128/DIG. 25

See application file for complete search history.

(56) References Cited

U.S. PATENT DOCUMENTS 1,672,114 A 6/1928 Crow
3,403,696 A * 10/1968 Pynchon ............... 137/516.13
3,783,454 A 1/1974 Sausse et al.
3,895,648 A * 7/1975 Stoll et al. ................ 137/550
4,225,979 A 10/1980 Rey et al.
4,258,705 A 3/1981 Sorensen et al.

(Continued)

FOREIGN PATENT DOCUMENTS

JP 08-068469 A * 3/1996 ................ 7/17

(Continued)

OTHER PUBLICATIONS

Hepperlen et al., "Self-Retained Internal Ureteral Stents: A New Approach," *The Journal of Urology*, Jun. 1978, vol. 119 (pp. 731-734).

(Continued)

*Primary Examiner*—Tatyana Zalukaeva
*Assistant Examiner*—Ilya Y Treyger
(74) *Attorney, Agent, or Firm*—Cooley Godward Kronish LLP

(57) ABSTRACT

An anti-reflux drainage device includes an elongated member defining a lumen, and a valve disposed along the elongated member. The valve can include one or more lumens in fluid connection with the lumen of the elongated member, a socket, a shaft disposed in the socket, and a stopper connected to the shaft that occludes the second lumen when exposed to retrograde pressure. Another such device includes an elongated member and a ball valve. The ball valve can include a seat and a shoulder defined by the elongated member, and a ball disposed in the elongated member between the seat and shoulder that occludes lumen when exposed to retrograde pressure.

25 Claims, 14 Drawing Sheets

U.S. PATENT DOCUMENTS

| | | | |
|---|---|---|---|
| 4,307,723 A | | 12/1981 | Finney |
| 4,334,327 A | | 6/1982 | Lyman et al. |
| 4,334,537 A | | 6/1982 | Peterson |
| 4,490,144 A | * | 12/1984 | Steigerwald ............. 604/323 |
| 4,550,749 A | * | 11/1985 | Krikorian ............... 137/843 |
| 4,560,375 A | * | 12/1985 | Schulte et al. ............. 604/9 |
| 4,623,348 A | | 11/1986 | Feit |
| 4,636,194 A | * | 1/1987 | Schulte et al. ............. 604/9 |
| 4,643,719 A | | 2/1987 | Garth et al. |
| 4,666,429 A | | 5/1987 | Stone |
| 4,846,816 A | | 7/1989 | Manfredi |
| 4,874,360 A | | 10/1989 | Goldberg et al. |
| 4,904,236 A | | 2/1990 | Redmond et al. |
| 4,931,037 A | | 6/1990 | Wetterman |
| 4,990,133 A | | 2/1991 | Solazzo |
| 5,019,102 A | | 5/1991 | Hoene |
| 5,030,199 A | | 7/1991 | Barwick et al. |
| 5,052,998 A | | 10/1991 | Zimmon |
| 5,112,301 A | | 5/1992 | Fenton, Jr. et al. |
| 5,116,309 A | | 5/1992 | Coll |
| 5,125,538 A | * | 6/1992 | Morris, Sr. ............... 222/143 |
| 5,234,409 A | | 8/1993 | Goldberg et al. |
| 5,352,182 A | | 10/1994 | Kalb et al. |
| 5,380,270 A | | 1/1995 | Ahmadzadeh |
| 5,514,109 A | | 5/1996 | Mollenauer et al. |
| 5,531,718 A | | 7/1996 | Sachse |
| 5,578,059 A | | 11/1996 | Patzer |
| 5,584,314 A | | 12/1996 | Bron |
| 5,599,291 A | | 2/1997 | Balbierz et al. |
| 5,647,843 A | | 7/1997 | Mesrobian et al. |
| 5,681,274 A | | 10/1997 | Perkins et al. |
| 5,743,872 A | | 4/1998 | Kelly |
| 5,782,916 A | | 7/1998 | Pintauro et al. |
| 5,855,478 A | * | 1/1999 | Van ........................ 433/95 |
| 5,860,449 A | * | 1/1999 | Schulte .................... 137/550 |
| 5,884,629 A | | 3/1999 | O'Brien |
| 5,941,703 A | * | 8/1999 | Van ........................ 433/95 |
| 5,984,965 A | | 11/1999 | Knapp et al. |
| 6,063,119 A | | 5/2000 | Pintauro et al. |
| 6,125,875 A | * | 10/2000 | Dempsey et al. .......... 137/217 |
| 6,149,125 A | | 11/2000 | Nilsson |
| 6,183,413 B1 | | 2/2001 | Migachyov |
| 6,189,859 B1 | | 2/2001 | Rohrbough et al. |
| 6,213,936 B1 | | 4/2001 | Nishioka et al. |
| 6,755,391 B2 | | 6/2004 | Newton et al. |
| 6,921,378 B2 | | 7/2005 | O'Keefe et al. |
| 2003/0018322 A1 | | 1/2003 | Tanghoj et al. |
| 2003/0060807 A1 | | 3/2003 | Tanghoj et al. |
| 2003/0163204 A1 | | 8/2003 | Rix |
| 2004/0138626 A1 | | 7/2004 | Cote et al. |
| 2004/0143328 A1 | | 7/2004 | Ginn |

OTHER PUBLICATIONS

Collier et al., "Proximal Stent Displacement as Complication of Pigtail Ureteral Stent," *Urology*, Apr. 1979, vol. XIII, No. 4 (pp. 372-375).

Mardis et al., "Polyethylene Double-Pigtail Ureteral Stents," *Urologic Clinics of North America*, Feb. 1982, vol. 9, No. 1 (pp. 95-101).

Patent Cooperation Treaty, Partial International Search Report, International Application No. PCT/US 02/27120, mailed on Dec. 12, 2002, 5 pages.

Patent Cooperation Treaty, International Search Report, International Application No. PCT/US 02/27120, mailed on Feb. 17, 2003, 9 pages.

* cited by examiner

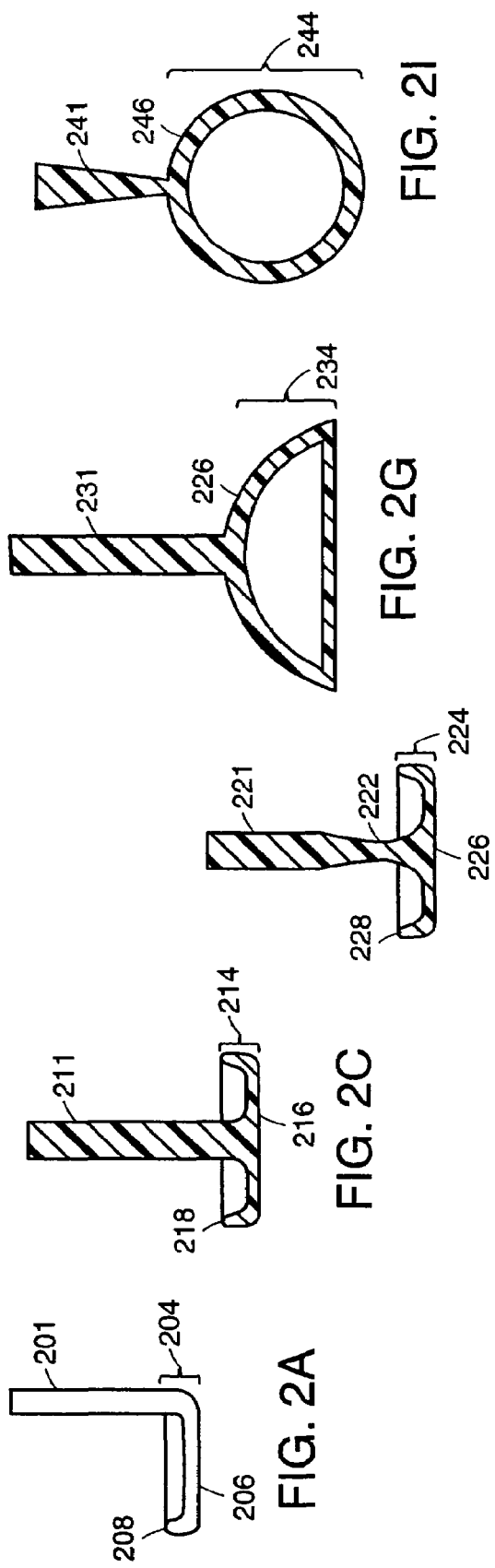

ANTI-REFLUX DRAINAGE DEVICES AND METHODS

This application is a continuation application of U.S. patent application Ser. No. 09/973,660, filed Oct. 9, 2001, and entitled ANTI-REFLUX DRAINAGE DEVICES AND METHODS, now U.S. Pat. No. 6,921,378, the entire content of which is hereby incorporated by reference.

TECHNICAL FIELD

Background Information

Drainage devices or stents may be used to treat or avoid obstructions in fluid passageways due to ureteral tumors that disrupt the flow of urine from the kidneys to the bladder. They also may be used to strengthen a compromised ureter wall. Ureteral stents typically are tubular in shape, terminating in two opposing ends: a kidney distal end and a bladder proximal end. One or both of the ends may be curved in a pigtail or J-shape to prevent the migration of the stent due, for example, to physiological movements.

SUMMARY OF THE INVENTION

Stents may cause or contribute to significant patient discomfort. One problem associated with ureteral stents is pain in the trigone that is attributed to stent contact with the trigone, particularly when the stent extends through the ureteral orifice and into the bladder. The region known as the trigone or trigonum is a triangular-shaped region located on the floor of the urinary bladder between the opening of the urethra in front and the two ureters at the sides. The trigone is believed to be particularly innervated and sensitive to the presence of any foreign bodies such as stent members. Another problem associated with ureteral stents is flank pain caused by urine reflux that occurs when urine travels from the bladder to the kidneys in response to retrograde pressure. Retrograde pressure occurs in the bladder when attempting to void the bladder of urine, and may transmit urine or other fluids up the stent to the kidney.

The present invention concerns a medical device that avoids patient discomfort caused by the device contacting the trigone and by urine flowing up the device toward the kidney. Patient discomfort induced by the use of a foreign body contacting the trigone may be minimized with devices that are small and flexible at the bladder end (proximal end) of the device and have little or no contact with the trigone. Urine reflux in the kidney may be decreased or avoided with devices that include a one-way valve to allow for drainage of urine from the kidney to the bladder, but not from the bladder to the kidney.

In one aspect, the invention relates to a medical device for assisting in the drainage of fluid from a body cavity. The device includes an elongated member that includes a distal end and a proximal end, and defines a lumen extending between the distal and proximal ends. The device also includes a valve disposed at the proximal end of the elongated member. The valve includes a tube defining a lumen in fluid connection with the lumen of the elongated member. The tube is connected to the proximal end of the elongated member. It includes a socket, a shaft at least partially disposed in the socket, and a stopper connected to the shaft that occludes the lumen when exposed to retrograde pressure.

The shaft may be fixed or axially translatable in the socket. The shaft may be tapered inwardly toward the stopper and the socket tapered inwardly toward the stopper, both preventing complete removal of the shaft from the socket. The valve may include a spring disposed in the socket that is biased to open the valve in the absence of a retrograde pressure. The tube may define one or more additional lumen in fluid connection with the first lumen, and the lumen may be disposed about the periphery of the socket The stopper may be constructed from a deformable film. The stopper may include a circular surface, and the shaft may be attached to the stopper at the center of the circular surface. The stopper may include a hemispherical surface, and the shaft may be attached to the stopper at the center of the hemispherical surface. The stopper may include a wedge-shaped section. The stopper may include a lip disposed about the periphery of its distal surface.

The device may be a stent, for example, a ureteral stent. The device may include a retention structure extending distally from the distal end of the elongated member. This retention structure may further define a passageway extending between an opening and the first lumen. The device also may include a retention structure extending from the stopper. This retention structure may be a lip disposed about a periphery of the stopper having a perimeter wider than the proximal end of the elongated member.

In another aspect, the invention relates to a valve for preventing reflux of fluids in a medical device. The valve includes a tube defining a lumen having a first end and a second end, and a socket. The valve also includes a shaft at least partially disposed in the socket, and a stopper attached to the shaft that occludes the lumen when exposed to retrograde pressure.

The shaft may be fixed or axially translatable in the socket. The shaft may be tapered inwardly toward the stopper and the socket tapered inwardly toward the stopper, both preventing complete removal of the shaft from the socket. The valve may include a spring disposed in the socket that is biased to open the valve in the absence of a retrograde pressure. The tube may define one or more additional lumen, and the lumen may be disposed about the periphery of the socket. The stopper may be constructed from a deformable film. The stopper may include a circular surface, and the shaft may be attached to the stopper at the center of the circular surface. The stopper may include a hemispherical surface, and the shaft may be attached to the stopper at the center of the hemispherical surface. The stopper may include a wedge-shaped section. The stopper may include a lip disposed about the periphery of its distal surface.

In yet another aspect, the invention relates to a method for assisting the drainage of fluid from a body cavity. The method includes the steps of providing a medical device and inserting it into a ureter. The device includes an elongated member having a distal end and a proximal end, and defining a first lumen extending between the distal and proximal ends. The device also includes a valve disposed at the proximal end of the elongated member. The valve includes a tube, a shaft and a stopper. The tube defines a second lumen in fluid connection with the first lumen, and is connected to the proximal end of the elongated member at a first end. The tube also defines a socket in which a shaft is at least partially disposed. The stopper is connected to the shaft and occludes the second lumen when exposed to retrograde pressure.

In yet another aspect, the invention relates to a medical device for assisting in the drainage of fluid from a body cavity. The device includes an elongated member having a distal end and a proximal end and defining a first lumen extending therebetween. The device also includes a seat defined by the elongated member, a shoulder defined by the elongated member proximal to the seat, and a ball disposed in the elongated member between the seat and the shoulder that occludes the first lumen when exposed to retrograde pressure.

The elongated member may define at least one slot between the seat and the shoulder. The device may include a retention structure defining a second lumen in fluid connection with the first lumen. The retention structure may have a pigtail shape. The shoulder may be defined by an interface between the elongated member and the retention structure. The device also may include a retention structure extending from the distal end of the elongated member. This retention structure may further define a passageway extending between an opening and the first lumen. The device may be a stent, for example, a ureteral stent.

In yet another aspect, the invention includes a method for preventing reflux of fluids in a medical device. The method includes providing a medical device and inserting it into a ureter. The medical device includes an elongated member having a distal end and a proximal end and defining a first lumen extending therebetween. The device further includes a seat defined by the elongated member, a shoulder defined by the elongated member proximal to the seat, and a ball disposed in the elongated member between the seat and the shoulder that occludes the first lumen when exposed to retrograde pressure.

The foregoing and other aspects, embodiments, features, and advantages of the invention will become apparent from the following description, figures, and claims.

BRIEF DESCRIPTION OF THE DRAWINGS

The drawings are not necessarily to scale, emphasis instead generally being placed upon illustrating the principles of the invention.

FIGS. 2A-B depict longitudinal cross-sectional and top views of a semicircular stopper and tubular shaft of the invention.

FIGS. 2C-D depict longitudinal cross-sectional and top views of a circular stopper and tubular shaft of the invention.

FIGS. 2E-F depict longitudinal cross-sectional and top views of a circular stopper and tapered shaft of the invention.

FIGS. 2G-H depict longitudinal cross-sectional and top views of a hemispherical stopper and tubular shaft of the invention.

FIGS. 2I-J depict longitudinal cross-sectional and top views of a spherical stopper and tapered shaft of the invention.

DESCRIPTION

This invention generally concerns a drainage device that, when positioned within a body passageway of a mammal, significantly reduces discomfort to the patient such as a ureteral stent positioned in the ureter of a human. The devices and methods of the present invention provide an increase in comfort for the patient by minimizing the degree of contact of the device with the trigone region, and reducing or eliminating reflux of liquid to the kidneys from the bladder.

One aspect of the present invention is a medical device for assisting in the drainage of fluid from a body cavity. One disclosed embodiment of the device includes an elongated member that includes a distal end and a proximal end, and defines a lumen extending between the distal and proximal ends. The device also includes a valve disposed at the proximal end of the elongated member. The valve includes a tube defining a lumen in fluid connection with the lumen of the elongated member. The tube is connected to the proximal end of the elongated member. It includes a socket, a shaft at least partially disposed in the socket, and a stopper connected to the shaft that occludes the lumen when exposed to the pressure differential experienced about the proximal end of the device that occurs, e g., during voiding. The pressure differential occurs when the pressure in the bladder increases relative to the pressure in the ureters and kidneys. This is referred to as backward or retrograde pressure. The valve occludes the lumen when exposed to retrograde pressure and thereby prevents urine from travelling from the bladder, through the lumen and into kidney.

The valve minimizes or prevents the flow of urine from the bladder to the kidneys when exposed to retrograde pressure in the bladder, while allowing urine to travel from the kidneys to the bladder in the absence of retrograde pressure. Generally, the stopper will occlude the lumen in the presence of retrograde pressure, and will not occlude the lumen in the absence of retrograde pressure. The valve stopper also may be large enough to prevent migration of the device through the ureteral orifice and up into the ureter. The stopper also may be shaped to minimize contact between the device and the trigone.

Figure 1A:
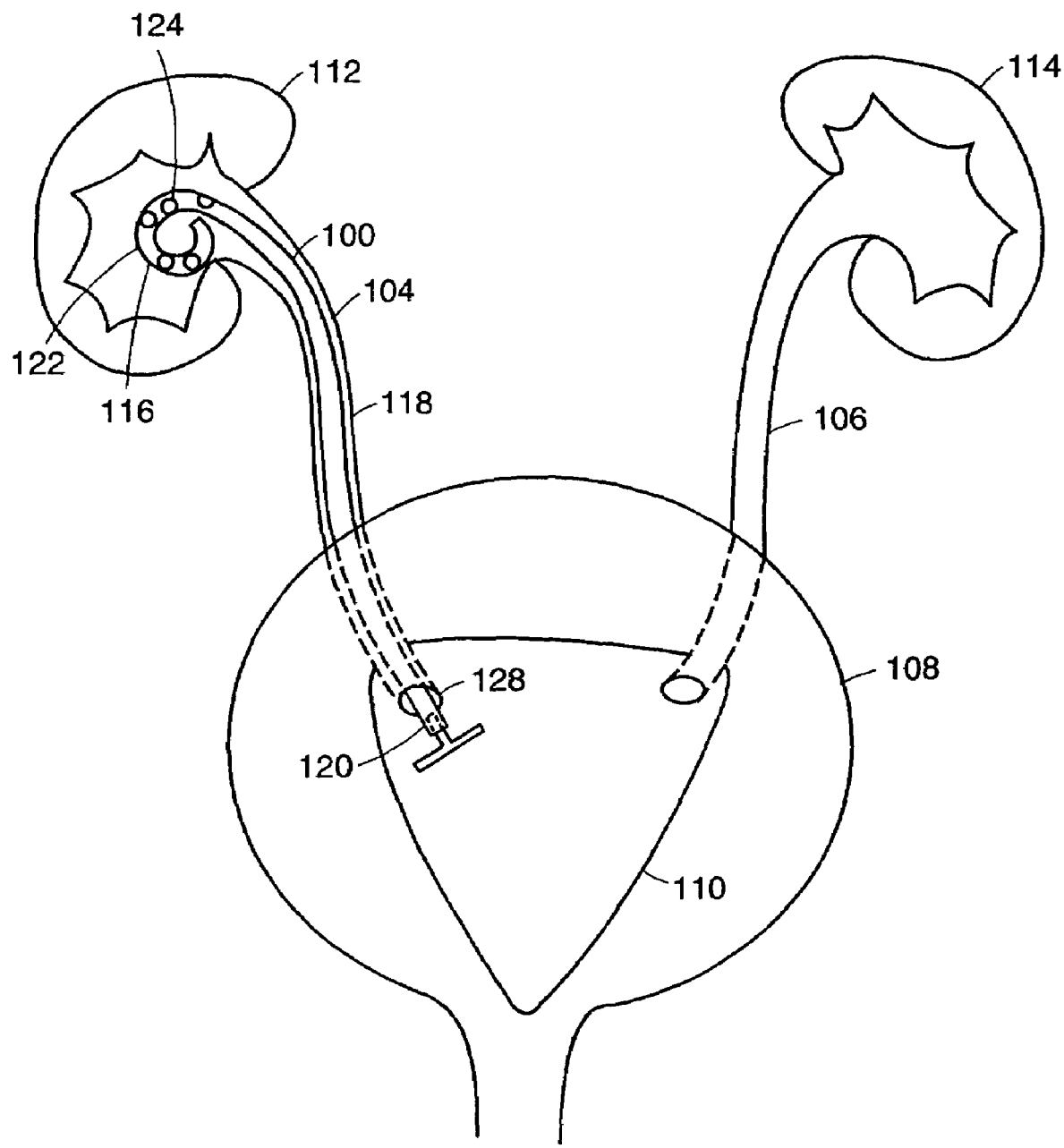
FIGS. 1A-F depict an exemplary embodiment of a medical device of the invention, with FIG. 1A showing a longitudinal cross-sectional view of a ureter, bladder and kidneys with a front view of the device positioned in the ureter with a distal region in a kidney and a proximal region in the bladder, FIG. 1B showing a front view of the device outside of the body, FIG. 1C showing a longitudinal cross-sectional view of the proximal portion of the device with a valve in an open position, FIGS. 1D and 1E showing transverse cross-sections of the device of FIG. 1C along lines D-D and E-E of FIG. 1C, respectively, and FIG. 1F showing a longitudinal cross-sectional view of the proximal portion of the device with a valve in a closed position.

Referring to FIG. 1A, when one or both of the ureters 104, 106 become blocked or weakened due to, for example, the growth of a tumor or trauma, a temporary fluid passageway is needed to provide fluid drainage from one or both of the kidneys 112, 114 to the bladder 108. A medical device 100 may be implanted to provide such a temporary fluid passageway. The device 100 is positioned in one of the ureters 104 with a distal end 116 in the corresponding kidney 112 and a proximal end 120 in the bladder 108.

Figure 1B:
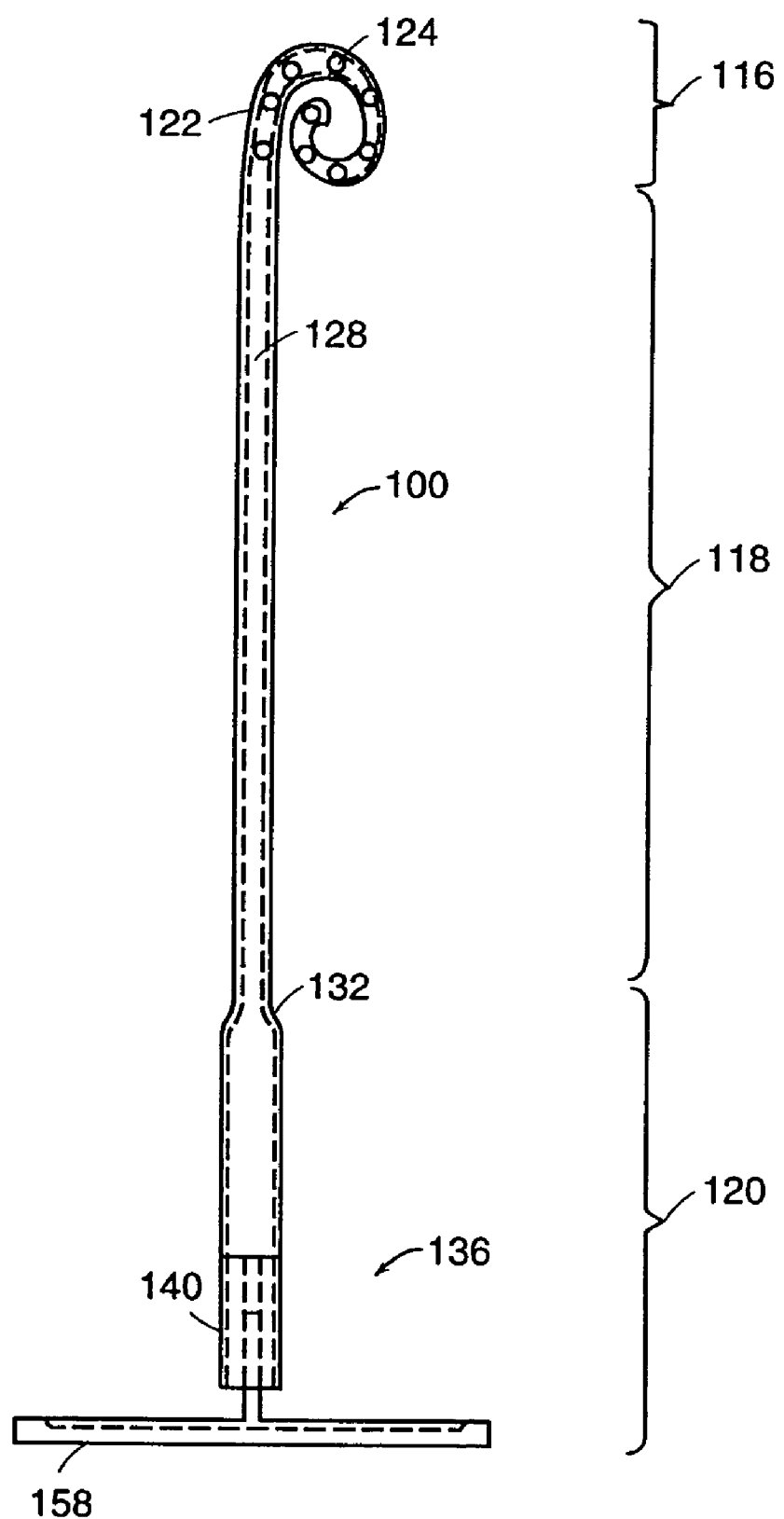

Referring to FIG. 1B, the device 100 includes an elongated member having an annular wall 132 that defines a lumen 128 extending from the distal end 116, through a middle region 118 to the proximal end 120. The middle region 118 is long enough to traverse the ureter 104 of the patient and extend from the distal end 116 positioned in the kidney 112 to the proximal end 120 positioned in the bladder 108.

The distal end 116 of the device 100 includes a retention structure 122 in the shape of a pigtail to retain the device 100 within the ureter 104, and prevent migration of the distal end 116 into the ureter 104. The retention structure 122 includes a plurality of openings 124 for the passage of fluid into the device 100. Suitable retention structures may be any of various geometries, such as the pigtail depicted in FIGS. 1A-B. They also may be hook or J-shaped. Suitable retention structures also may have slots or openings in them for the drainage of fluid. The cross-sectional geometry of the annular wall of the elongated member may be any shape that allows the flow of liquid through the segment including, for example, round, oblong, elliptical, hexagonal, D-shaped, crescent-shaped and square.

Figure 1C:
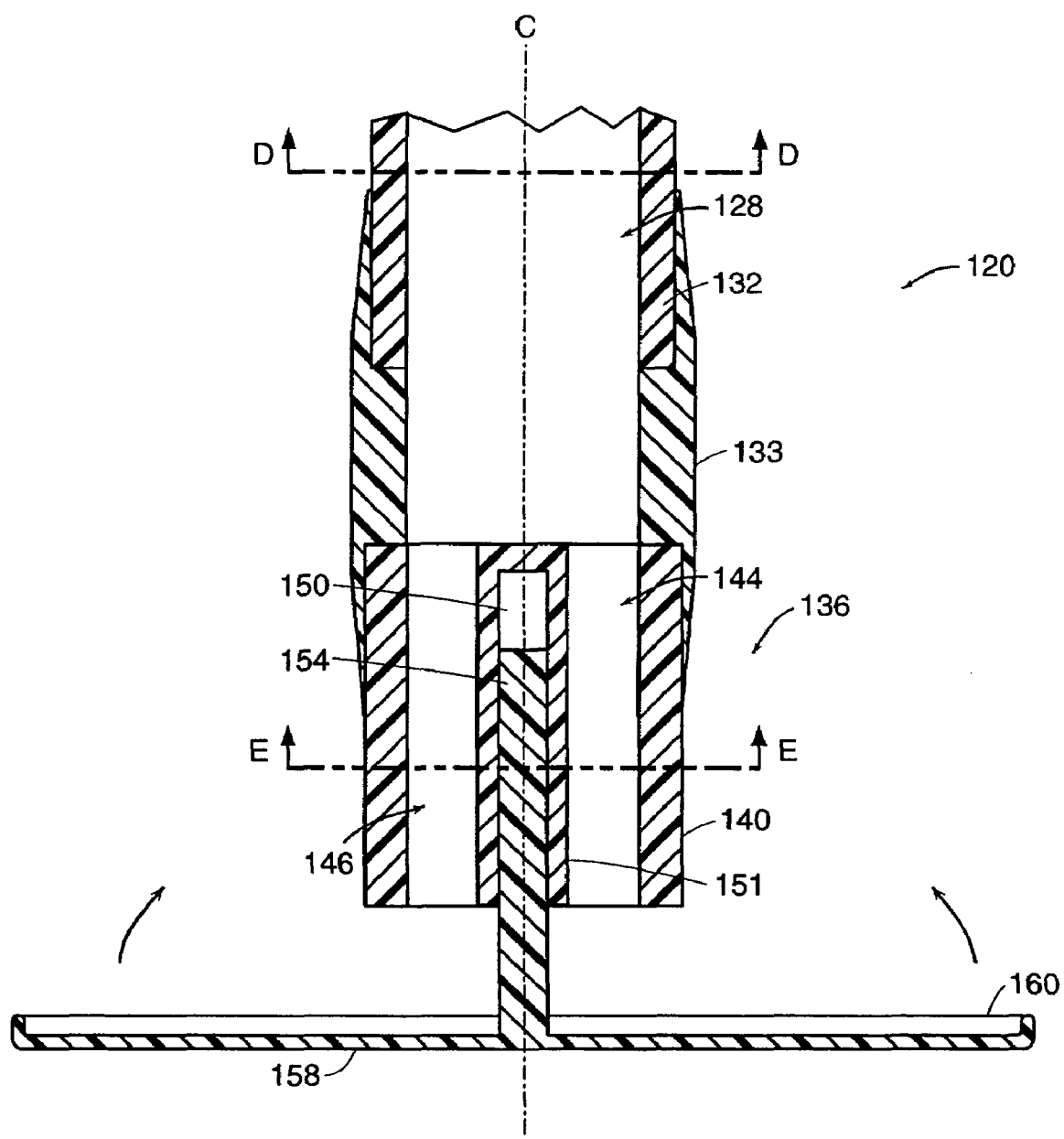
Figure 1D:
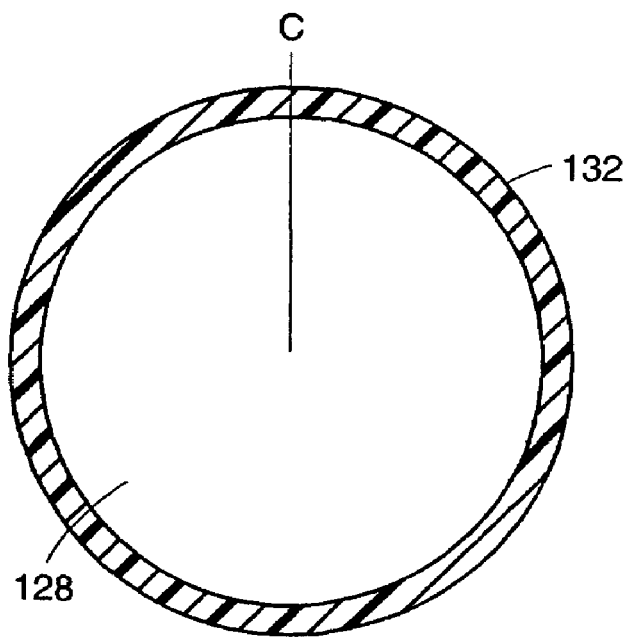
Figure 1E:
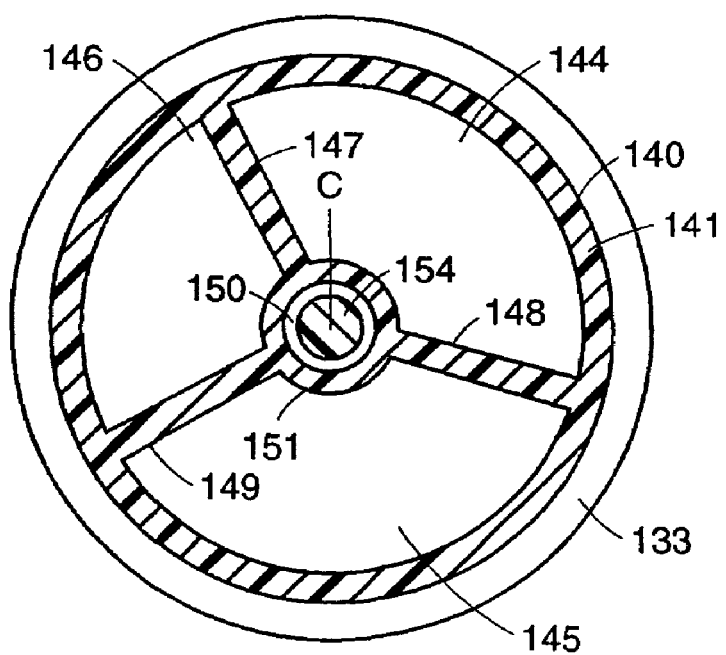
Figure 1F:
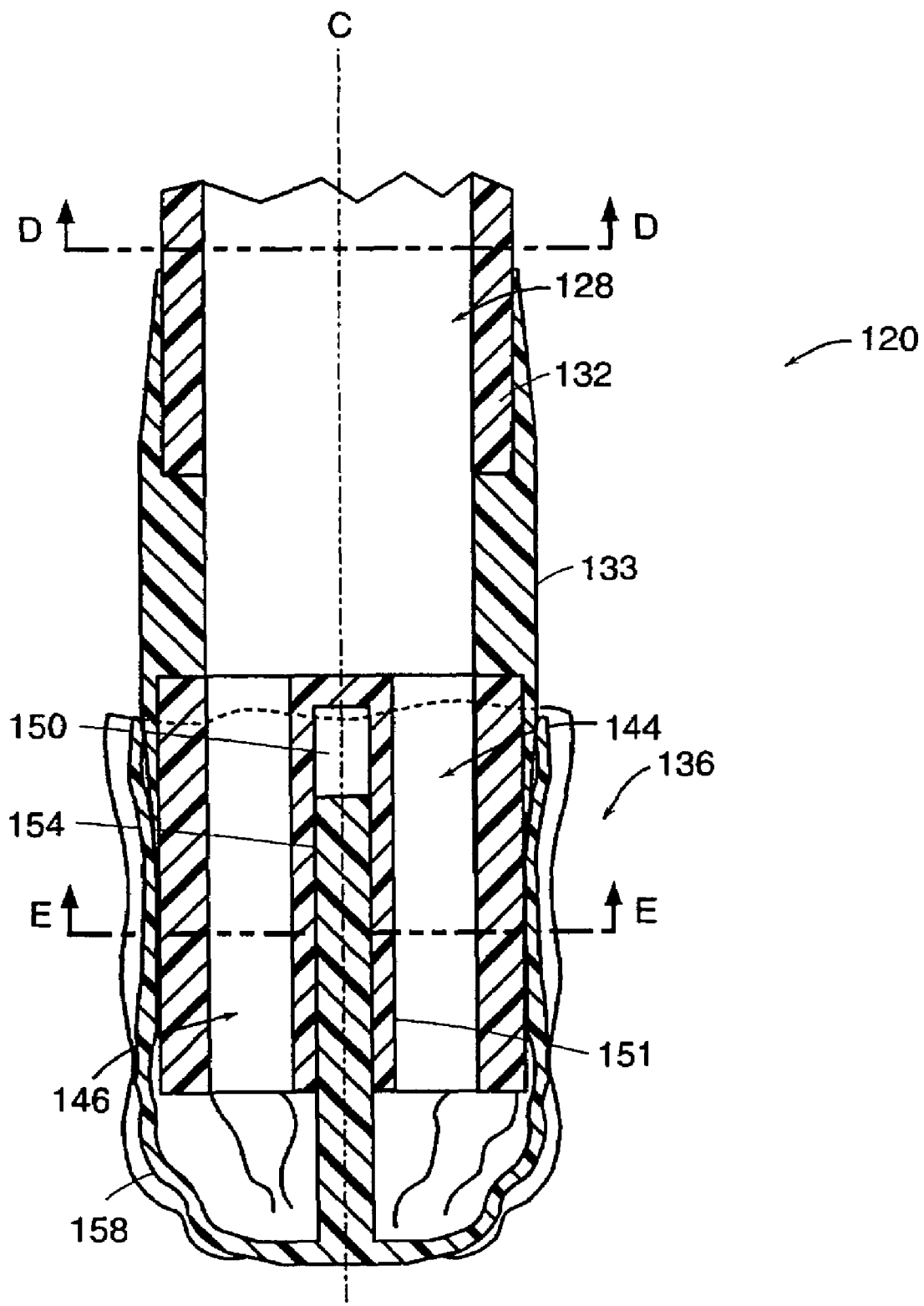

Referring to FIGS. 1B-F, the medical device 100 further includes a valve 136 disposed at the proximal end 120. The valve 136 generally includes a tube 140 having three lumens 144, 145, 146 defined by an outer wall 141, an inner wall 151 and three side walls 147, 148, 149. The lumens 144, 145, 146 are in fluid connection with the lumen 128. The valve 136 is connected to the annular wall 132 of the device by a wall 133. The valve 136 also includes a shaft 154 that is at least partially disposed in a socket 150 defined by the inner wall 151, and a stopper 158 connected to the shaft 154. The stopper 158 occludes the lumens 144, 145, 146 when exposed to retrograde pressure. The valve stopper 158 is large enough to act as a retention structure and prevent migration of the proximal portion 120 through the ureteral orifice 128 and up into the ureter 104, and is shaped to minimize its contact with the trigone 110. The stopper 158 also includes a lip 160 that generally retains the shape of the stopper 158 when the valve 136 is not exposed to retrograde pressure as shown in FIG. 1C. The valve stopper 158 is constructed from a readily deformable layer or film, e.g., a thin polymer film, so that it readily deforms in the presence of retrograde pressure to block the passage of urine into the lumens 144, 145, 146 as shown in FIG. 1F. In this embodiment, the shaft 154 is fixed in the socket 150 by adhesive (not shown). The shaft 154 can also be fixed by other methods such as by heat welding or by a snap fitting the shaft 154 into the inner wall 151.

The shaft and stopper may take on a variety of forms, including, for example, those depicted in FIGS. 2A-J. FIG. 2A is a longitudinal cross-sectional view of a tubular shaft 201 connected to a stopper 204. The stopper 204 includes a substantially planar portion 206 and a lip 208. The planar portion 206 is semicircular or wedge-shaped as shown in FIG. 2B (top view), and may be used, for example, in a valve that has a socket on the periphery of the outer wall such as that depicted in FIG. 3B and discussed below. The walls of the shaft 201 are parallel and circular in cross-section, although other configurations may be suitable such as, for example, the shaft may be tapered and/or the cross-section may be oblong, elliptical, hexagonal, D-shaped, crescent-shaped or square in cross-section. Also, the planar portion 206 has a 180° wedge-shape, but it may have a wedge-shape with a smaller or larger angle such as, for example, a 90° wedge-shape (not shown) or a 270° wedge-shape (not shown). FIG. 2C is a longitudinal cross-sectional view of a tubular shaft 211 connected to a stopper 214. The stopper 214 includes a substantially planar portion 216 and a lip 218. The planar portion 216 is substantially circular in shape as shown in FIG. 2D (top view), and the shaft 211 is attached to the center of the circular surface of the planar portion 216. The shaft 211 and the stopper 214 may be used, for example, in a valve that has a socket located along the central axis of a valve such as those depicted in FIGS. 3A and 3C and discussed below. The walls of the shaft 211 are parallel and circular in cross-section, although other configurations may be suitable such as, for example, the shaft may be tapered and/or the cross-section may be oblong, elliptical, hexagonal, D-shaped, crescent-shaped or square in cross-section. FIG. 2E is a longitudinal cross-sectional view of a tubular shaft 221 connected to a stopper 224. The shaft 221 includes a taper in both directions from a portion 222. The stopper 224 includes a substantially planar portion 226 and a lip 228. The planar portion 226 is circular in shape as shown in FIG. 2F (top view), and the shaft 221 is attached to the center of the circular surface of the planar portion 226. The shaft 221 and the stopper 224 may be used, for example, in a valve that has a socket located along the central axis of a valve such as those depicted in FIGS. 3A and 3C and discussed below. The walls of the shaft 221 are parallel and circular in cross-section, although other configurations may be suitable such as, for example, the shaft may be untapered or tapered in only one direction and/or the cross-section may be oblong, elliptical, hexagonal, D-shaped, crescent-shaped or square in cross-section. FIG. 2G is a longitudinal cross-sectional view of a shaft 231 connected to a stopper 234. The stopper 234 includes a hollow substantially hemispherical portion 226 as shown in FIGS. 2G-H that is open on the end opposite the shaft 231. The shaft 231 is attached to the stopper 234 at the center of the proximal surface of a substantially hemispherical portion 226. This stopper may be used, for example, in a valve that has a socket located along the central axis of the valve such as those depicted in FIGS. 3A and 3C and discussed below. The walls of the shaft 231 are parallel and circular in cross-section, although other configurations may be suitable such as, for example, the shaft may be tapered and/or the cross-section may be oblong, elliptical, hexagonal, D-shaped, crescent-shaped or square in cross-section. FIGS. 2I and 2J are longitudinal cross-section and top views, respectively, of a shaft 241 connected to a stopper 244. The shaft 241 includes a taper towards the stopper 244. The stopper 244 includes a hollow substantially spherical portion 246. This stopper may be used, for example, in a valve that has a socket located along the central axis of the valve such as those depicted in FIGS. 3A and 3C and discussed below. The walls of the shaft 241 are tapered in one direction and substantially circular in cross-section, although other configurations may be suitable such as, for example, the shaft may be untapered or tapered in two directions and/or the cross-section may be oblong, elliptical, hexagonal, D-shaped, crescent-shaped or square in cross-section.

Figure 5A:
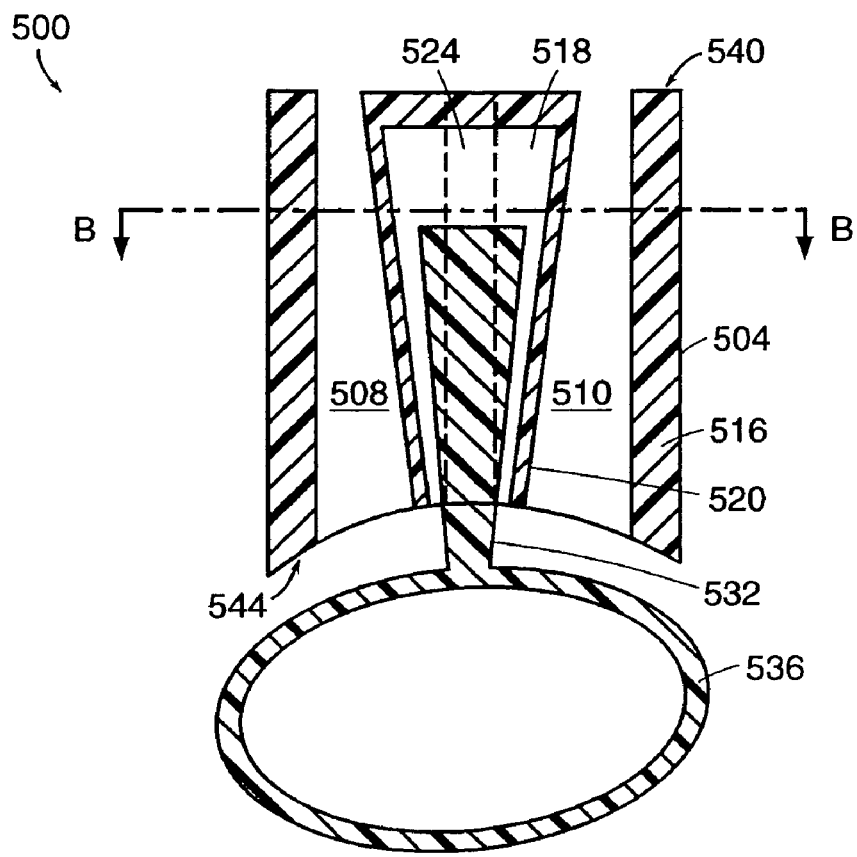
FIG. 5A-B depict longitudinal and transverse cross-sectional views, respectively, of an exemplary embodiment of a valve of the invention.
Figure 5B:
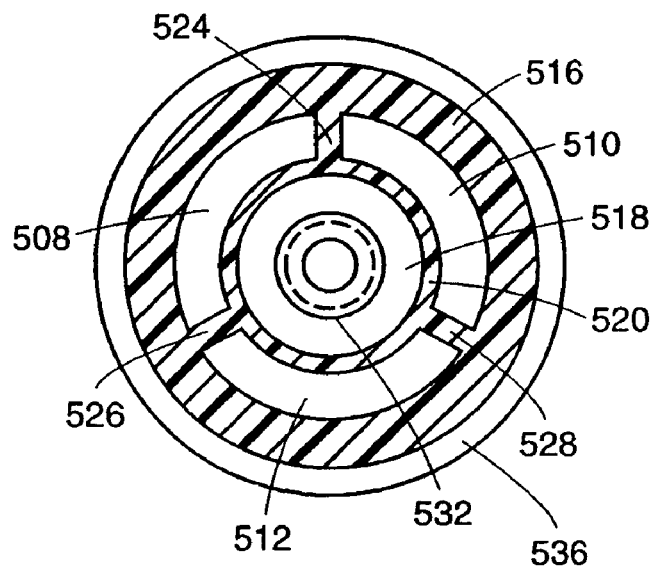

Stoppers suitable for use in accordance with the present invention may have various other shapes. For example, it may be substantially ellipsoidal as depicted in FIGS. 5A-B and discussed below. The lip may maintain the general shape of the stopper yet be pliable enough so that it doesn't cause discomfort when contacting the trigone region. The lip may also aid in the prevention of reflux if the stopper is planar and the lip extends distally and toward the tube. The stoppers may have rounded corners so to minimize protrusion into the bladder wall, particularly in the sensitive trigone region. The stopper may be large enough to prevent migration of the proximal end of the device through the ureteral orifice and into the ureter.

The shaft may be fixed or axially translatable in the socket. The shaft may be fixed in the socket by, e.g., an adhesive, a snap fit or a heat weld. In the embodiments where the shaft is fixed in the socket, the stopper may be readily collapsible such that it occludes the lumen of the device when exposed to retrograde pressure from the bladder to the kidney. For example, the stopper may be constructed from a deformable polymer or plastic film that collapses towards the proximal end of the tube when the bladder pressurizes in an attempt to void so that urine cannot enter the lumen of the valve, travel up the lumen of the elongated member and enter the kidney. The stopper may further include a lip that is resilient or has shape memory properties about the outer edge of the stopper so that the stopper shape is generally regained and retained when the bladder is not pressurized.

In embodiments where the shaft is axially translatable in the socket, the shaft and socket may have opposite tapers toward the stopper to prevent complete removal of the shaft from the socket. Additionally or alternatively, the shaft may include a spring located in the socket disposed on the distal end of the shaft that is biased to open the valve in the absence of retrograde pressure by axially translating the stopper away from the proximal end of the tube.

In embodiments where the shaft and socket are not tapered, the valve may include alternative designs to prevent complete removal of the shaft from the socket. For example, a short tether or a spring may be attached to both the shaft and a socket wall. The socket also may include a ridge formed near the opening at the proximal end of the valve and the shaft may also contain a ridge about its distal end, such that both ridges abut one another in an expanded or open configuration and the shaft cannot be removed completely from the socket.

Figure 3A:
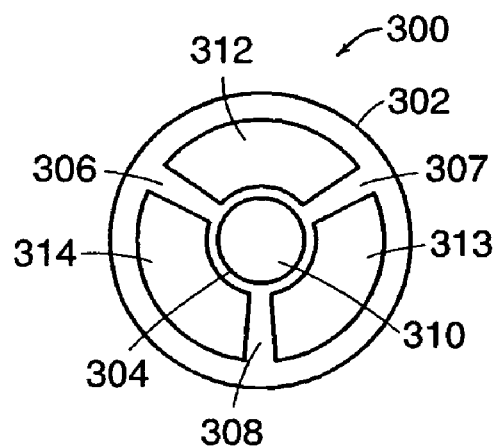
FIGS. 3A-C depict proximal views of various exemplary embodiments of a tube for inclusion in a devices of the present invention.
Figure 3B:
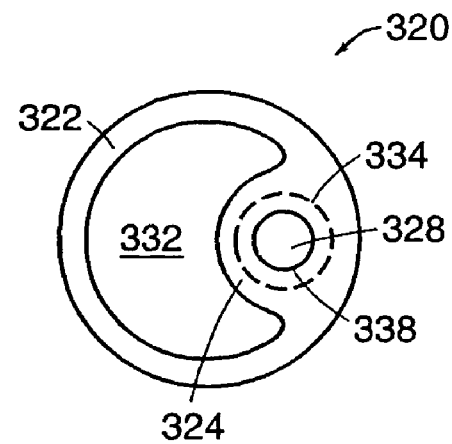
Figure 3C:
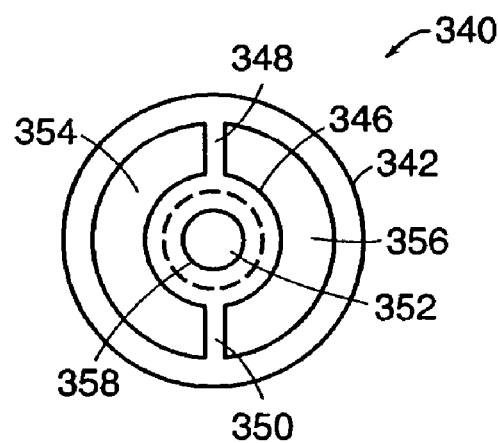

The tube may include more than one lumen in fluid connection with the lumen of the elongated member and take on a variety of internal geometries. FIGS. 3A-C depict proximal views of various exemplary embodiments of a tube for inclusion in valves of the present invention. FIG. 3A depicts a triple lumen tube 300 that includes an outer annular wall 302, an inner annular wall 304 and three walls 306, 307, 308. The inner annular wall 304 defines a socket 310 disposed at the center of the tube 300. The walls 302, 304, 306, 307 and 308 define three symmetrical lumens 312, 313, 314 surrounding the socket 310. FIG. 3B depicts a single tube 320 that includes an outer annular wall 322 and a wall 324. The walls 322, 324 define a lumen 332 and a socket 328 that tapers inwardly from a distal end 334 to a proximal opening 338. FIG. 3C depicts a dual lumen tube 340 that includes an outer annular wall 342, an inner annular wall 346 and two walls 348, 350 both extending from the outer annular wall 342 to the inner annular wall 346. The walls 342, 346, 348, 350 define two symmetrical lumens 354, 356 surrounding a socket 352 disposed at the center of the tube 340. The inner annular wall 346 defines the socket 352 and a lip 358. The lip 358 may retain a shaft that also has a lip on the exterior surface on or near its distal end that has a diameter greater than that of the lip 358 but less than that of the socket 352. It can be appreciated that the tube may include further lumens and/or can take on additional internal geometries.

Figure 4:
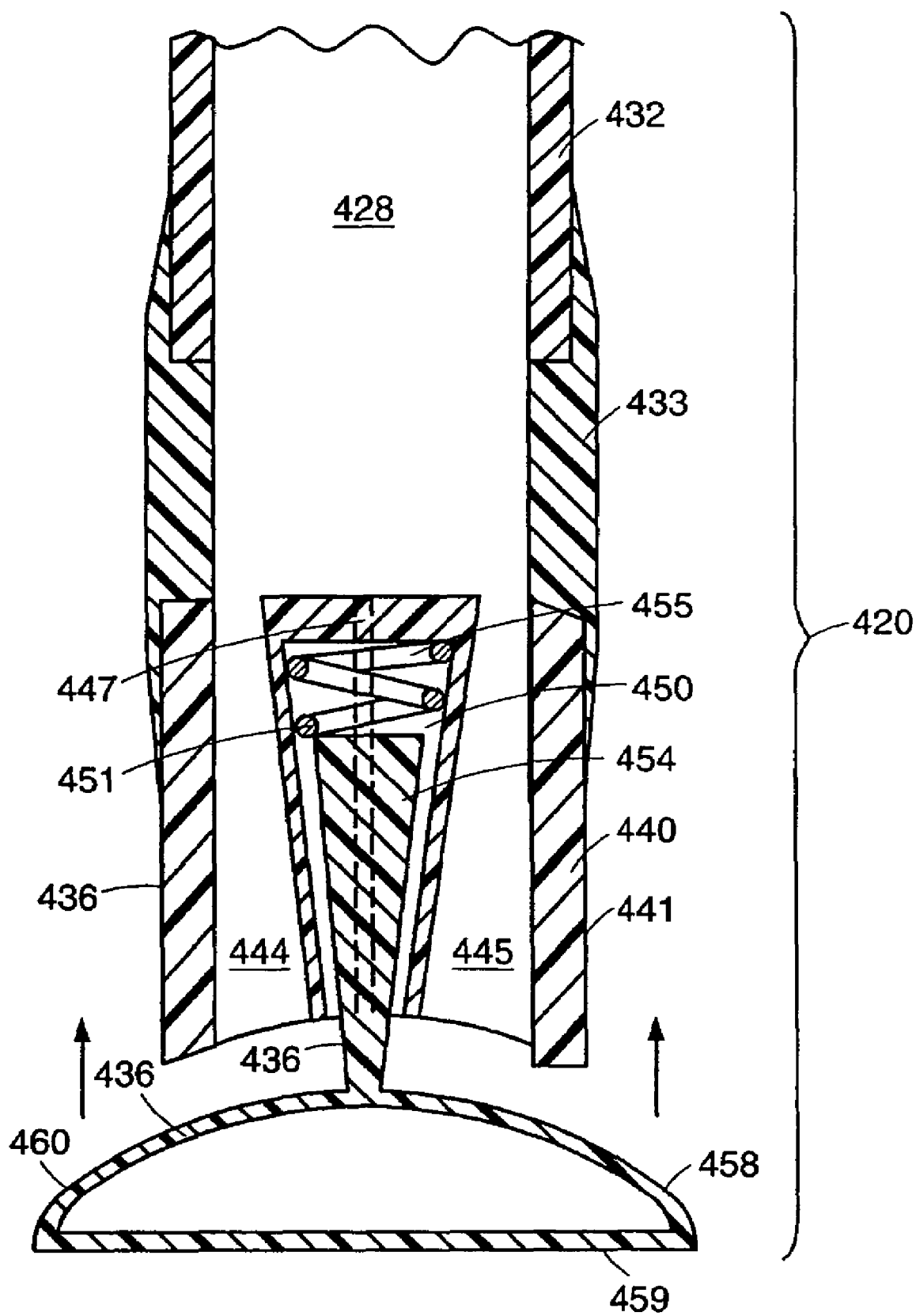
FIG. 4 depicts a longitudinal cross-sectional view of another exemplary embodiment of a proximal region of a medical device of the invention.

FIG. 4 depicts a longitudinal cross-sectional view of another exemplary embodiment of a proximal end 420 of a medical device of the invention. The proximal end 420 includes a lumen 428 defined by a wall 432 that extends to the distal end (not shown) of the medical device. The wall 432 is attached to a valve 436 by an annular wall 433. The valve 436 includes a tube 440 having two lumens 444, 445. The lumens 444, 445 are defined by an outer wall 441, an inner wall 451, a wall 447 extending from the outer wall 441 to the inner wall 451, and a wall 448 (not shown) located opposite the wall 447 extending from the inner wall 451 to the outer wall 441. The lumens 444, 445 are in fluid connection with the lumen 428.

The inner wall 451 also defines a socket 450. Disposed within the socket 450 is a spring 455 and a shaft 454. The socket 450 and the shaft 454 are tapered inwardly towards their proximal ends such that the shaft 454 is axially translatable in the socket 450, but cannot be completely removed from the socket 450. The stopper 458 includes a hollow substantially hemispherical portion 460 that is open on its proximal end, and a lip 459 about the periphery of the open end of the stopper 458. The shaft 454 is attached on its proximal end to the center of the distal surface of the hemispherical portion 460 of the stopper 458.

The valve stopper 458 is large enough to prevent migration of the valve through a ureteral orifice (not shown), and is constructed from a flexible polymer. The valve stopper 458 is shown in the open position. When exposed to retrograde pressure in the bladder, the pressure axially translates the stopper 458 and the shaft 454 into the socket 450 and against the bias of the spring 455 in the direction of the arrows such that it occludes the lumens 444, 445 and does not allow the passage of urine into the lumen 428. After voiding and in the absence of retrograde pressure, the spring 455 translates the stopper 458 and the shaft 454 proximally into an open position such that the stopper 458 no longer occludes the lumens 444, 445, and urine traveling from the distal end of the device may pass through the lumens 428, 444, 445 and exit the proximal end 420 of the device into the bladder.

The device optionally may include a retention structure extending proximally from the stopper if the stopper is not large enough to function as a retention device. The retention structure may be a lip provided about the periphery of the stopper that is larger than the proximal end of the elongated member. Devices of the present invention also may include an extraction thread that may be embedded in the wall of the proximal region of the elongated member, in the valve along the tube, in a shaft wall, or in the stopper. An extraction thread is a graspable structure for removal of the device from the body.

Another aspect of the present invention is a valve for preventing reflux of fluids in a medical device. Valves of the present invention generally include a tube defining a lumen having a first end and a second end, and a socket. The valve also includes a shaft at least partially disposed in the socket, and a stopper attached to the shaft that occludes the lumen when exposed to retrograde pressure. Such valves have been described in connection with the medical devices depicted in FIGS. 1-4 above, and further include the valve depicted in FIGS. 5A-B.

FIGS. 5A-B depict longitudinal and transverse cross-sectional views, respectively, of an exemplary embodiment of a valve 500 of the invention. FIG. 5B is taken along line B-B shown in FIG. 5A. The valve 500 generally includes a tube 504, a shaft 532 and a stopper 536. The tube 504 having a first end 540 and a second end 544, defines three lumens 508, 510, 512 and a socket 518. The lumens 508, 510, 512 are defined by an outer wall 516, an inner wall 520 and three walls 524, 526, 528 extending from the inner wall 520 to the outer wall 516. The shaft 532 and the socket 518 are tapered inwardly toward the stopper 536, such that the shaft 532 cannot be completely removed from the socket 518, but is axially translatable therein. The stopper 536 is hollow and substantially ellipsoidal in shape, but may have any of the shapes described herein, including, but not limited to, those depicted and described in connection with FIGS. 1-4. The shaft 432 is circular in cross section and tapered but may have any of the configurations described herein, including, but not limited to, those depicted and described in connection with FIGS. 1-4

When the second end 544 of the tube 504 is exposed to pressure, for example, a retrograde pressure, the stopper 536 and the shaft 532 are axially translated into the socket 518 such that the stopper 536 occludes the lumens 508, 510, 512, and does not allow the passage of fluids, such as blood or urine, through the valve 500. In the absence of pressure on the second end 544, pressure from fluid passing from the first end 540 of the valve 500 into the lumens 508, 510, 512 axially translates the stopper 532 and the shaft 536, such that the stopper 532 no longer occludes the lumens 508, 510, 512. Fluids may thus pass from the first end 540 of the tube 504 and exit the second end 544, but is blocked from flowing in the opposite direction.

Valves of the present invention may be incorporated into a variety of medical devices where one-way flow is desirable to assist in the drainage of fluid. Valves of the present invention may include any of the aspects described above in connection with valves incorporated into medical devices having an elongated member.

Yet another aspect of the present invention includes a medical device for assisting in the drainage of fluid from a body cavity that generally includes a ball valve located along an elongated member. The device minimizes or prevents fluid reflux in the presence of a retrograde pressure, and minimizes contact with the trigone.

Figure 6A:
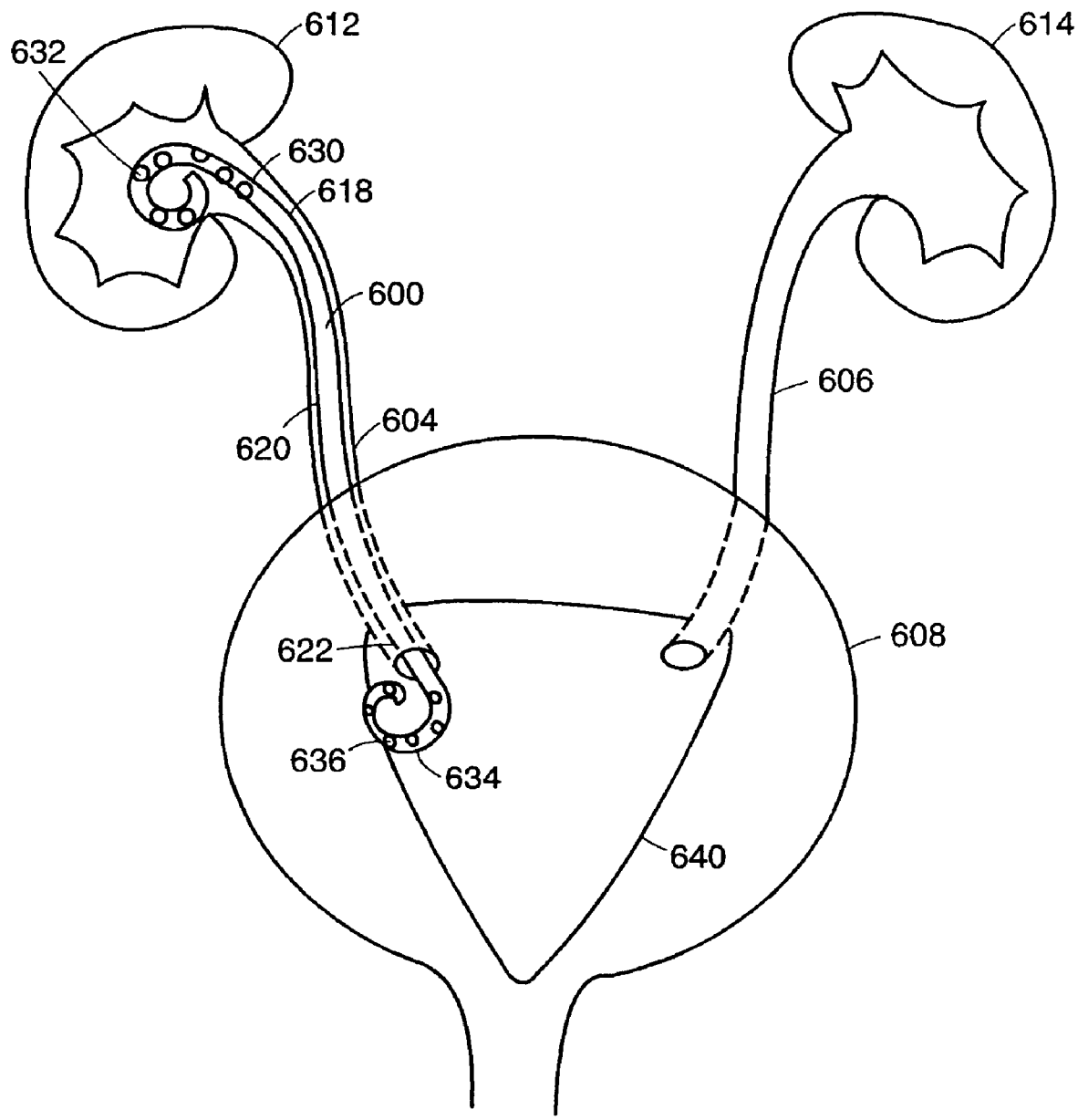
FIGS. 6A-C depict yet another exemplary embodiment of a medical device of the invention, with FIG. 6A showing a longitudinal cross-sectional view of a ureter, bladder and kidneys with a front view of the device positioned in the ureter with a distal region in a kidney and a proximal region in the bladder, FIG. 6B showing a front view of the device outside of the body, and FIG. 6C showing a longitudinal cross-sectional view of the proximal portion of the device.
Figures 6B, 6C:
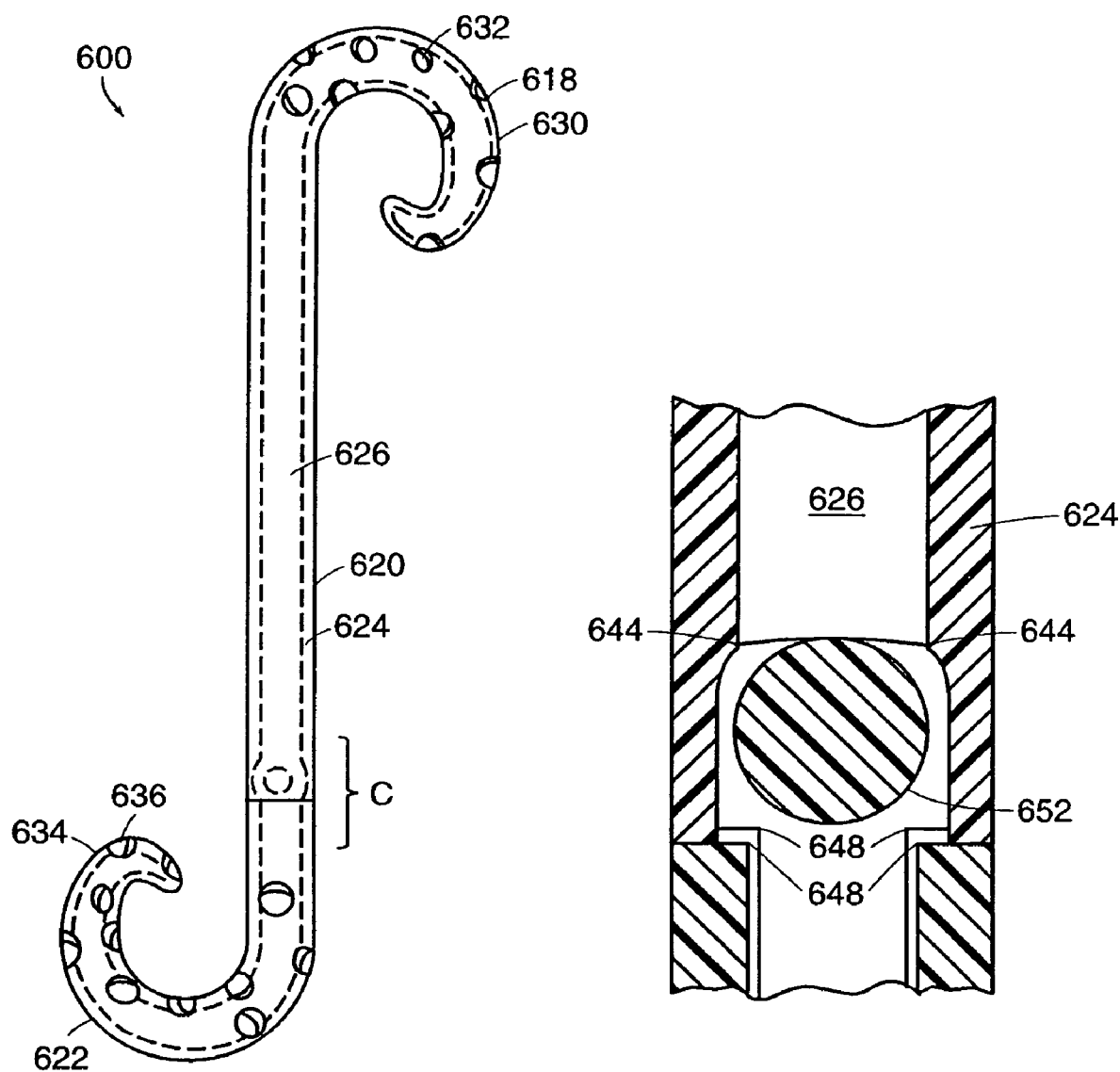

FIGS. 6A-C depict yet another exemplary embodiment of a medical device 600 of the invention. FIG. 6A shows a longitudinal cross-sectional view of two ureters 604, 606, a bladder 608 and a kidneys 612, 614 with a front view of the device 600 positioned in the ureter 604 with a distal end 618 in the corresponding kidney 612, and a proximal end 622 in the bladder 608. FIG. 6B shows a front view of the device 600 outside of a body. FIG. 6C shows a longitudinal cross-sectional view of a portion of the proximal end 622 indicated by the bracket C in FIG. 6B.

When one or both of the ureters 604, 606 become blocked or weakened due to, for example, the growth of a tumor, removal of a tumor or trauma to the ureters, a temporary fluid passageway is desirable to provide fluid drainage from one or both of the kidneys 612, 614 to the bladder 608. The medical device 600 may be implanted in one or both kidneys to provide such a temporary passageway.

The device 600 includes an elongated member having a distal end 618, a middle region 620, and a proximal end 622 having a wall 624 that defines a lumen 626. The elongated member is long enough to traverse the ureter 604 of the patient and extend on the distal end 618 into the kidney 612, and on the proximal end 622 into the bladder 608. In the embodiment shown in FIGS. 6A-C, a pigtail 630 is located at the distal end 618 and a pigtail 634 is located at the proximal end 622 of the device 600. The pigtail 630 retains the distal end 618 in the kidney 612, and includes a plurality of openings 632 for the passage of fluid from the kidney 612 into the lumen 626. The pigtail 634 retains the proximal end 620 of the device 600 in the bladder 608, and includes a plurality openings 636 for the passage of fluid from lumen 626 to the bladder 608. The pigtail 634 is shaped and positioned in the bladder 608 to minimize contact with the trigone 640.

Referring to FIG. 6C, the device 600 includes a seat 644 defined by a wall 624, and a shoulder 648 defined by the wall 624 located proximally to the seat 644. The device 600 further includes a spheroidal ball 652 disposed in the lumen 626 between the seat 644 and the shoulder 648. When exposed to retrograde pressure in the bladder 608, the ball 652 is translated distally against the seat 644 thus occluding the lumen 626. When retrograde pressure is absent, pressure from fluid in the lumen 626 flowing from the kidney 612 and through the lumen 626 translates the ball 652 away from the seat 644 allowing passage of fluid around the ball 652 to the pigtail 634. The shoulder 648 retains the ball 652 within the lumen 626 but does not impede the flow of fluid. In this embodiment, the shoulder 648 includes elements that project into the lumen 626 and prevent the ball 652 from passing to the proximal end 622 of the device 600, while allowing fluid to flow past the shoulder 648 to the proximal end 622 of the device 600. The shoulder 648 also can include slots (not shown) that allow fluid to flow proximally past the shoulder 648 into the proximal end 622 of the device.

Figure 7A:
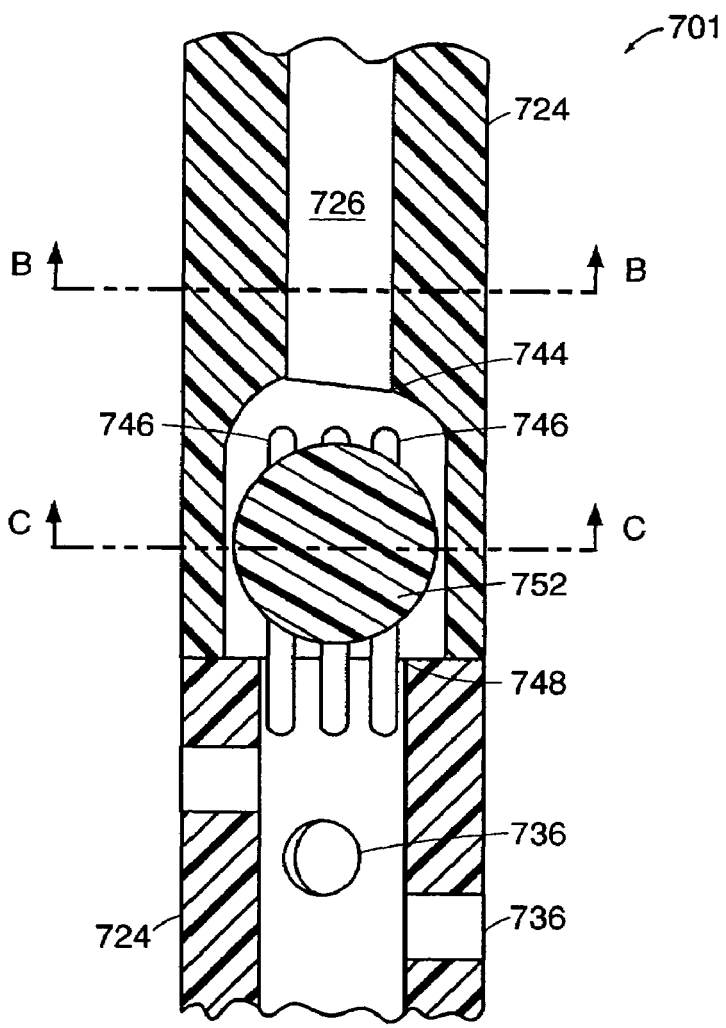
FIGS. 7A-C depict another exemplary embodiment of a proximal end of a medical device of the present invention, FIG. 7A showing a longitudinal cross-section, and FIGS. 7B and 7C showing transverse cross-sections of the proximal end of the device of FIG. 7A along lines B-B and C-C, respectively.
Figure 7B:
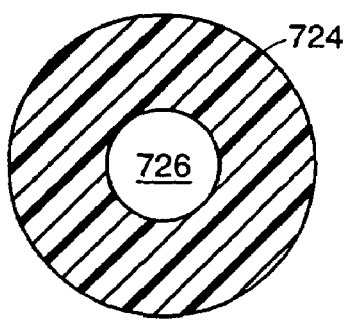
Figure 7C:
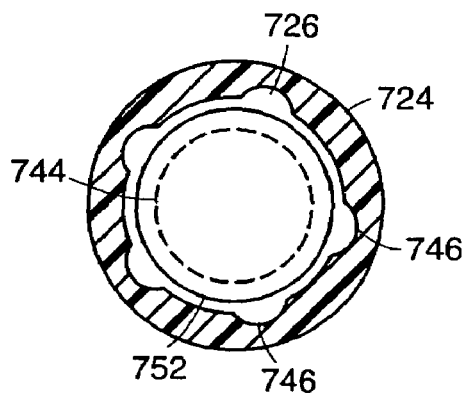

FIGS. 7A-C depict another exemplary embodiment of a proximal end 701 of a medical device of the present invention, FIG. 7A showing a longitudinal cross-section, and FIGS. 7B and 7C showing transverse cross-sections of the proximal end 701 of the device of FIG. 7A along lines B-B and C-C, respectively.

The proximal end 701 includes a seat 744 and a shoulder 748 defined by a wall 724. The shoulder 748 is located proximally to the seat 744. The wall 724 also defines a lumen 726. The proximal end 701 further includes a spheroidal ball 752 disposed in the lumen 726 between the seat 744 and the shoulder 748. When exposed to retrograde pressure, the ball 752 is translated distally against the seat 744 thus occluding the lumen 726. When retrograde pressure is absent, pressure from fluid in the lumen 726 flowing from the proximal end of the lumen 726 translates the ball 752 away from the seat 744 allowing passage of fluid around the ball 752. The fluid passage is facilitated by a plurality of slots 746 defined by the wall 724 located proximally to the seat 744. The fluid passes around the ball 752 and out of the proximal end 701 through the openings 736 in the wall 724. The shoulder 748 retains the ball 752 within the lumen 726 but does not impede the flow of fluid, which can flow through the slots 746 that extend through the shoulder 748.

Retention structures may be any of various geometries, such as the pigtails. They may also be hooks, J-shaped or malecots. They may have slots or openings in them for the drainage of fluid. The devices of the present invention also may include an extraction thread embedded in the wall of the proximal region of the elongated member.

The cross-sectional geometry of the annular wall of the elongated member may be any shape that allows the flow of liquid through the segment including round, oblong, elliptical, hexagonal, D-shaped, crescent-shaped, square, for example. Slots defined by the wall may be of various shapes and depths. For example, the slots may be straight, curved, or helical along the wall and have a polygonal or curved cross-section. The slots may also pass through the shoulder.

Another aspect of the present invention is a method for assisting the drainage of fluid from a body cavity. This method generally includes providing a medical device as described above and inserting the device into a ureter. The device may be inserted from the kidney or the bladder.

The device may be inserted with the aid of a guide wire with a pusher through the urethra and urinary bladder to the final position in the ureter. The guide wire or a cannula may be used to temporarily straighten the retention structure in the distal region. The distal region is constructed from material that reforms its structure after having its shape distorted. This property of the material comprising the distal region allows for the retention structure at the distal region to be straightened during insertion of the stent into the body and still allowing the retention structure to reform into its original shape. The device may also be inserted into position by use of an endoscope, a ureteroscope, or a cytoscope, for example. Once the stent is located in the ureter it must be positioned so that the distal region is properly seated in the renal pelvis and the proximal end is located in the urinary bladder.

Figure 8A:
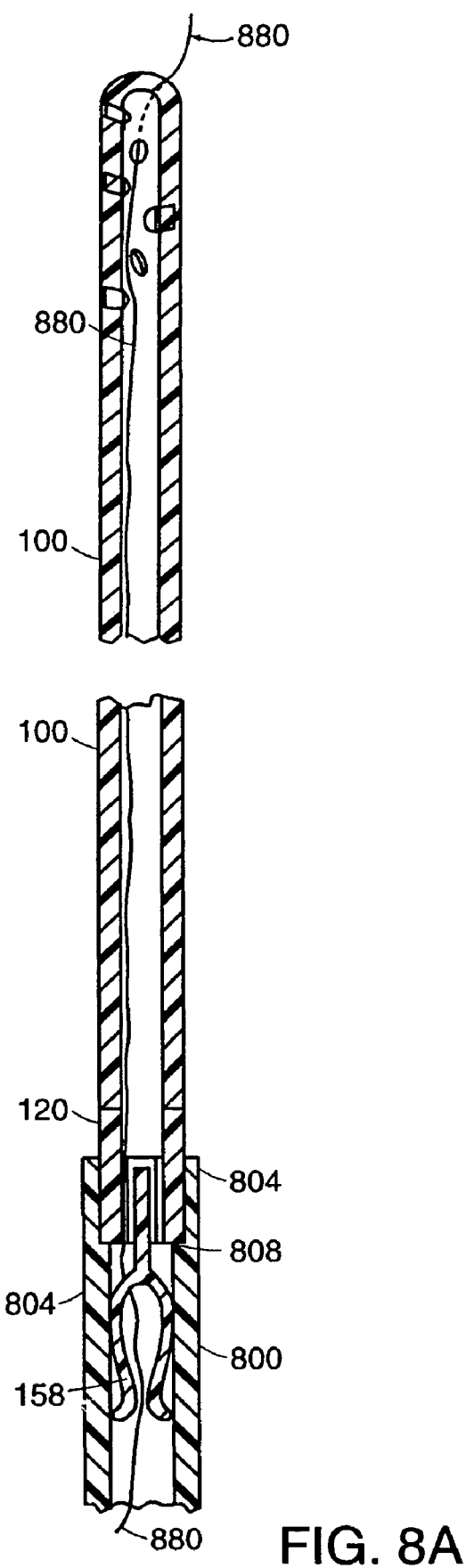
FIGS. 8A-B depict longitudinal cross-sectional views of two embodiments of insertion devices of the present invention, each contacting a medical device of the invention, as occurs during installation of the medical device, with FIG. 8A showing an insertion device contacting the medical device depicted in FIGS. 1A-E, and FIG. 8B showing an insertion device contacting the medical device depicted in FIGS. 6A-C.
Figure 8B:
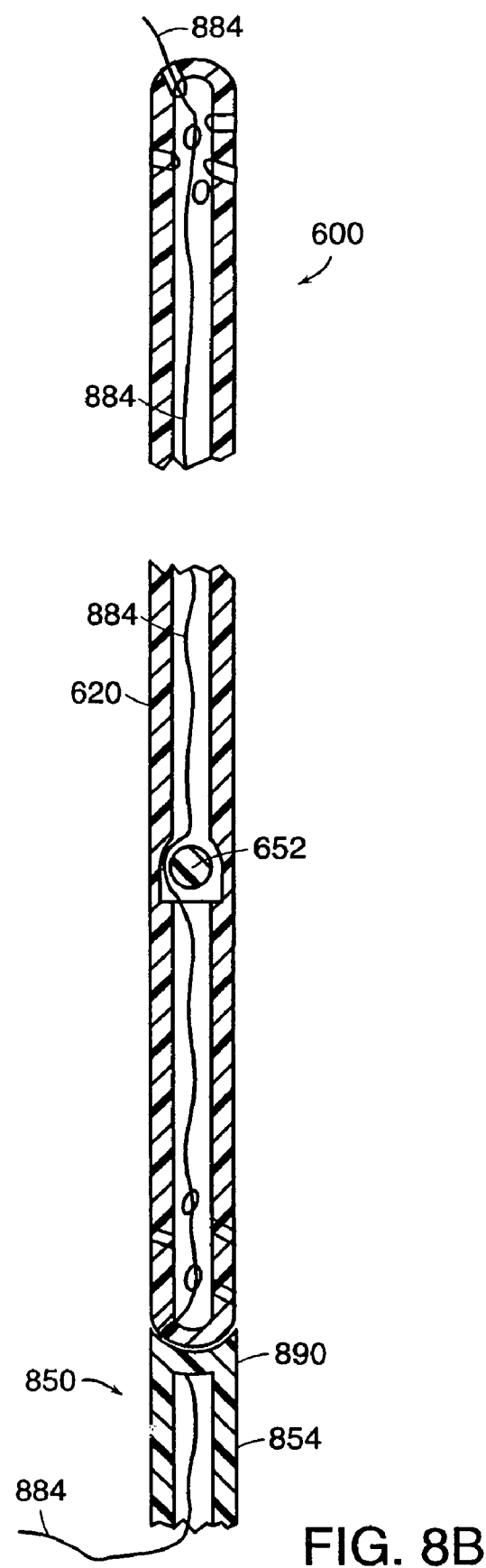

FIGS. 8A-B depict longitudinal cross-sectional views of two embodiments of insertion devices 800, 850 of the present invention, each contacting a medical device of the invention, as occurs during installation of the medical device. FIG. 8A shows an end of the insertion device 800 contacting the medical device 100 depicted in FIGS. 1A-E. FIG. 8B shows an end of the insertion device 850 contacting the medical device 600 depicted in FIGS. 6A-C.

Referring to FIG. 8A, a sleeve 804 encloses a stopper 158 of the device 100. The stopper 158 is temporarily folded as shown during the insertion of the device 100 into a patient's body. The shoulder 808 defined by the sleeve 804 abuts and applies a force against the proximal end 120 of the device 100 to push it into the body of the patient during installation of the device 100. After insertion of the device 100, the insertion device 800 is removed from the body and the stopper 158 unfolds as shown in FIG. 1A. The stoppers of the present invention, for example, the stoppers shown in FIGS. 2A-J and FIGS. 5A-B, may be similarly collapsed into the sleeve on an insertion device for insertion into the body.

Referring to FIG. 8B, a distal end 890 of a pusher 854 abuts and applies a force against the proximal end 620 of the medical device 600 to push it into the body of the patent during installation of the medical device 600. The distal end 890 of the pusher 854 is adapted to fit the proximal end 620 of the medical device 600 so that force applied to the pusher 854 during installation may be effectively transferred to the medical device 600.

The two guidewires 880, 884 shown in FIGS. 8A and B, respectively, may function to assist in the installation of the devices of the present invention. For example, the guidewire may be inserted into the body, travelling through the urinary bladder and ureter until reaching the kidneys and the renal pelvis. Once the guidewire is in the body, the device is inserted into the body by inserting the proximal end of the guidewire into the lumen of the distal end of the device and by moving the device along the length of the guidewire, by the use of a pusher. The pusher may include a lumen that is configured to accept a guidewire.

Another aspect of the present invention is a method of making a medical device for assisting in the drainage of fluid from a body cavity. The method includes providing one or more polymers, and forming a medical device from the one or more polymers. The polymers may be biocompatible plastics or polymers including ethylene vinyl acetate (EVA), polytetrafluoroethylene (PTFE), silicone polyurethane, polyurethane plastics, polyethylene plastics, and thermoplastic elastomers, for example. The polymer may have a Shore A hardness between about 60A and 85A or 35D and 65D. Check balls, such as those depicted in FIGS. 6A-C and FIGS. 7A-C may be constructed from any glass or plastic. Suitable plastics include nylons, such as nylon 12, and polytetrafluoroethylene. Preferably, the check ball is constructed from a material that is lubricious. Polymer membranes or foils for use as stoppers, such as that depicted in FIG. 1A, may be constructed from a polymer, such as nylon 12. It may have a thickness of between about 0.0001 to about 0.05 inches, preferably between about 0.01 and about 0.015 inches.

Various techniques, such as, for example, machining, injection molding, compression molding, dip molding, extrusion, and thermosetting may be used to manufacture the device of the present invention. Parts may be machined by providing a material that changes its mechanical characteristics from rigid to elastic with temperature or hydration.

Elements of the devices of the present invention may be attached to each other by any of a variety of methods including, for example, the use of adhesives, heat welding, mechanical fasteners and/or inserting one component into the internal diameter of the other. For example, two elements may be formed, one with a female end and one with a male end with teeth stamped therein, so that when the male end is inserted into the female end, it is locked or snap-fit into position with the teeth. Retention devices, such as pigtails, hooks and/or lips, may be memory shaped so that the devices may be temporarily straightened for insertion along a guidewire and thereafter retain its shape.

Elements of the devices of the present invention may be constructed as one piece or more than one piece and then attached to each other. For example, to construct the device depicted in FIGS. 6A-C, the pigtails and the middle region may be constructed separately and then welded together after inserting the ball between the middle region and the proximal pigtail. The wall of the middle region may be molded to define the seat, and the union between the proximal pigtail and the middle region may define the shoulder.

The devices may have walls of constant or varying thickness. Preferably, portions of the walls in the distal or kidney region are sufficiently thick to be kink-resistant despite constriction or other manipulation of the device due to enlargement of tissue surrounding it or peristaltic motions, and during insertion and removal of the device into the body. A kink resistant stent wall has an annular wall that does not collapse upon itself upon radial or lateral pressure of the surrounding body tissue when positioned to drain a body cavity of a mammal or upon longitudinal pressure exerted during insertion of the stent into the body cavity. Kink resistant properties may be imparted to a stent by varying the thickness of the wall of the stent depending on the softness or sturdiness of the material used to manufacture the stent. For example, a wall thickness of from about 0.008 inch to about 0.03 inch may be used with materials such as silicone, EVA, PTFE, polyurethane plastics, and polyethylene plastics. The inside wall diameter may be between about 0.035 inch to about 0.12 inch, preferably is between about 0.035 inch and 0.075 inch, and most preferably is about 0.06 inch. The outside wall diameter may be between about 0.05 inch and about 0.120 inch, preferably is between about 0.05 inch and about 0.10 inch, and most preferably is between about 0.08 inch and about 0.09 inch.

Having thus described certain embodiments of the present invention, various alterations, modifications, and improvements will be apparent to those of ordinary skill. Such alterations, modifications, and improvements are intended to be within the spirit and scope of the invention. Accordingly, the foregoing description of illustrative embodiments of the invention is not intended to be limiting.

What is claimed is:

1. A valve for preventing reflux of fluids in a ureteral stent comprising:
   a tube having a first end, a second end, and a socket disposed at the second end, the tube defining a length extending along a central axis from the first end of the tube to the second end of the tube, the tube defining a lumen extending from the first end of the tube to the second end of the tube, the lumen having a length substantially equal to the length defined by the tube;

a shaft having a proximal end and a distal end, the distal end of the shaft being disposed in the socket; and a stopper attached to the proximal end of the shaft and movable between a first position in which the stopper does not occlude the lumen and a second position in which the stopper occludes the lumen, the stopper moving from the first position to the second position in response to retrograde pressure in a bladder of a patient, the stopper having a lip configured to bias the stopper in the first position.

2. The valve of claim 1, wherein the stopper includes a deformable film.

3. The valve of claim 1, wherein
the lumen is a first lumen,
the tube further defining a second lumen, the first lumen and the second lumen being disposed about the periphery of the socket.

4. The valve of claim 1, wherein the socket defines a length substantially equal to the length defined by the tube.

5. The valve of claim 1, wherein the stopper is configured to retain at least a portion of the valve within the bladder of the patient when the stopper is in the first position.

6. The valve of claim 1, wherein the tube further comprises an outer surface and an inner surface, the stopper contacting the outer surface of the tube when in the second position.

7. The valve of claim 1, wherein the lip is made of shape memory material.

8. The valve of claim 1, wherein the lip is made of a resilient material.

9. The valve of claim 1, wherein the shaft is fixedly coupled to the socket such that the shaft has a position with respect to the socket when the stopper is in the first position, the shaft being in the position with respect to the socket when the stopper is in the second position.

10. The valve of claim 1, wherein the socket is fludically isolated from the lumen.

11. A valve for preventing reflux of fluids in a ureteral stent comprising:
a tube having a first end, a second end, and a socket, the tube defining a length extending along a central axis from the first end of the tube to the second end of the tube, the tube defining a lumen extending from the first end of the tube to the second end of the tube, the lumen having a length substantially equal to the length defined by the tube, the socket being fludically isolated from the lumen;
a shaft coupled to the socket, the shaft defining a proximal end and a distal end, the distal end of the shaft being disposed in the socket; and
a stopper attached to the shaft having a first, undeformed configuration in which the stopper does not occlude the lumen and a second, deformed configuration in which the stopper occludes the lumen, the stopper deformable from the first configuration to the second configuration in response to retrograde pressure in a bladder of a patient.

12. The valve of claim 11, wherein the stopper includes a deformable film.

13. The valve of claim 11, wherein
the lumen is a first lumen,
the tube further defining a second lumen, the first lumen and the second lumen being disposed about the periphery of the socket.

14. The valve of claim 11, wherein the stopper has a distal surface with a periphery, the stopper includes a lip disposed about the periphery of the distal surface.

15. The valve of claim 11, wherein the socket defines a length substantially equal to the length defined by the tube.

16. The valve of claim 11, wherein an outer diameter of the stopper is greater than an outer diameter of the tube.

17. The valve of claim 11, wherein the tube further comprises an outer surface and an inner surface, the stopper contacting the outer surface of the tube when in the second position.

18. The valve of claim 11, wherein the shaft is fixedly coupled to the socket such that the shaft has a position with respect to the socket when the stopper is in the first position, the shaft being in the position with respect to the socket when the stopper is in the second position.

19. The valve of claim 11, wherein the stopper has a lip configured to bias the stopper in the first position.

20. A valve for preventing reflux of fluids in a ureteral stent comprising:
a tube defining a lumen having a first end and a second end, the tube having an outer surface, an inner surface, and an outer diameter;
a shaft defining a proximal end and a distal end, the distal end of the shaft being coupled to an inner wall of the tube; and
a stopper coupled to the shaft and having a first configuration in which the stopper does not occlude the lumen and a second configuration in which the stopper occludes the lumen, the stopper having a diameter greater than the outer diameter of the tube, the diameter of the stopper being large enough to help retain at least a portion of the valve within the bladder of the patient when in the first configuration, the stopper configured to move from the first configuration to the second configuration in response to retrograde pressure in the bladder of the patient, the stopper contacting the outer surface of the tube while in the second configuration.

21. The valve of claim 20, wherein the stopper includes a deformable film.

22. The valve of claim 20, wherein
the lumen is a first lumen,
the inner wall of the tube defines a socket,
the tube further defining a second lumen, the first lumen and the second lumen being disposed about the periphery of the socket.

23. The valve of claim 20, wherein the stopper has a distal surface with a periphery, the stopper includes a lip disposed about the periphery of the distal surface.

24. The valve of claim 20, wherein the shaft is fixedly coupled to the socket such that the shaft has a position with respect to the tube when the stopper is in the first configuration, the shaft being in the position with respect to the tube when the stopper is in the second configuration.

25. The valve of claim 20, wherein the stopper has a lip configured to bias the stopper in the first position.

* * * * *